(12) United States Patent
Oser et al.

(10) Patent No.: US 8,617,089 B2
(45) Date of Patent: Dec. 31, 2013

(54) INDUCING TACTILE STIMULATION OF MUSICAL TONAL FREQUENCIES

(75) Inventors: Richard Barry Oser, Lafayette, CO (US); Suzannah Long, Lafayette, CO (US)

(73) Assignee: So Sound Solutions LLC, Louisville, CO (US)

( * ) Notice: Subject to any disclaimer, the term of this patent is extended or adjusted under 35 U.S.C. 154(b) by 98 days.

(21) Appl. No.: 13/171,614

(22) Filed: Jun. 29, 2011

(65) Prior Publication Data

US 2011/0257468 A1 Oct. 20, 2011

Related U.S. Application Data

(60) Division of application No. 11/463,520, filed on Aug. 9, 2006, now Pat. No. 7,981,064, which is a continuation-in-part of application No. 11/061,924, filed on Feb. 18, 2005, now Pat. No. 7,418,108.

(60) Provisional application No. 60/706,718, filed on Aug. 9, 2005.

(51) Int. Cl.
*A61H 1/00* (2006.01)

(52) U.S. Cl.
USPC .............. 601/47; 601/46; 601/57; 601/56; 601/49; 601/48

(58) Field of Classification Search
USPC .......... 601/47, 2, 15, 46, 48, 49, 56, 57, 58, 601/59, 61; 381/423, 424, 429, 182, 186, 381/396, 152, 300; 181/144, 147, 199
See application file for complete search history.

(56) References Cited

U.S. PATENT DOCUMENTS

| | | | |
|---|---|---|---|
| 2,297,972 A | 10/1942 | Mills |
| 2,520,172 A | 8/1950 | Rubinstein |
| 2,821,191 A | 1/1958 | Paii |
| 2,862,069 A | 11/1958 | Marchand |
| 2,980,108 A | 4/1961 | Scott |
| 3,366,749 A | 1/1968 | Ries |
| 3,430,007 A | 2/1969 | Thielen |
| 3,524,027 A | 8/1970 | Thurston |

(Continued)

FOREIGN PATENT DOCUMENTS

WO WO 03/092441 11/2003

OTHER PUBLICATIONS

U.S. Appl. No. 60/546,021, filed Feb. 19, 2004.
U.S. Appl. No. 60/652,611, filed Feb. 14, 2005.

(Continued)

*Primary Examiner* — Justine R Yu
*Assistant Examiner* — Colin W Stuart
(74) *Attorney, Agent, or Firm* — Willim W. Cochran; Cochran Freund & Young LLC

(57) ABSTRACT

Transducers and resonators are embedded in body support structures in contact with a user to for the purpose of conveying musical sound energy to a user's body at selected frequencies and in selected patterns. Body support structures include beds, pillows, chairs, and other structures typically used to support people. The sound may be audio tones and/or music. The transducers and resonators may be incorporated into a foam component or in a coil spring component of the body support structure. Latex-type foams and beds made with springs are candidate body support structures for receiving transducer's and resonators. Electro-active polymers are also used as transducers.

6 Claims, 14 Drawing Sheets

(56) References Cited

U.S. PATENT DOCUMENTS

| | | | |
|---|---|---|---|
| 3,556,088 | A | 1/1971 | Leonardini |
| 3,567,870 | A | 3/1971 | Rivera |
| 3,728,497 | A | 4/1973 | Komatsu |
| 3,763,853 | A | 10/1973 | Jochimski |
| 3,880,152 | A | 4/1975 | Nohmura |
| 4,020,299 | A | 4/1977 | Garner et al. |
| 4,023,566 | A | 5/1977 | Martinmaas |
| 4,055,170 | A | 10/1977 | Nohmura |
| 4,064,376 | A | 12/1977 | Yamada |
| 4,124,249 | A | 11/1978 | Abbeloos |
| 4,344,422 | A | 8/1982 | Immel |
| 4,354,067 | A | 10/1982 | Yamada et al. |
| 4,635,287 | A | 1/1987 | Hirano |
| 4,750,208 | A | 6/1988 | Yamada et al. |
| 4,753,225 | A | 6/1988 | Vogel |
| 4,757,548 | A * | 7/1988 | Fenner, Jr. .......... 381/189 |
| 4,813,403 | A | 3/1989 | Endo |
| 4,841,587 | A | 6/1989 | Carter et al. |
| 4,951,270 | A | 8/1990 | Andrews |
| 4,967,871 | A | 11/1990 | Komatsubarra |
| 5,007,410 | A | 4/1991 | Delaney |
| 5,014,687 | A | 5/1991 | Raffel |
| 5,018,518 | A | 5/1991 | Hubner |
| 5,035,235 | A * | 7/1991 | Chesky ............ 601/47 |
| 5,086,755 | A | 2/1992 | Schmid-Eliber |
| 5,097,821 | A | 3/1992 | Eakin |
| 5,101,810 | A | 4/1992 | Skille et al. |
| 5,143,055 | A | 9/1992 | Eakin |
| 5,187,398 | A | 2/1993 | Stuart et al. |
| 5,216,769 | A | 6/1993 | Eakin |
| 5,255,327 | A | 10/1993 | Endo |
| 5,314,403 | A | 5/1994 | Shaw |
| 5,341,054 | A | 8/1994 | Tal et al. |
| 5,368,359 | A | 11/1994 | Eakin |
| 5,424,592 | A | 6/1995 | Bluen et al. |
| 5,437,607 | A | 8/1995 | Taylor |
| 5,437,608 | A * | 8/1995 | Cutler ............... 601/49 |
| 5,442,710 | A | 8/1995 | Komatsu |
| 5,473,700 | A | 12/1995 | Fenner, Jr. |
| 5,624,155 | A | 4/1997 | Bluen et al. |
| 5,784,733 | A | 7/1998 | Rasamny et al. |
| 5,898,244 | A | 4/1999 | Kotsianas et al. |
| 6,024,407 | A | 2/2000 | Eakin |
| 6,027,463 | A * | 2/2000 | Moriyasu ........... 601/46 |
| 6,104,820 | A * | 8/2000 | Soza ............... 381/151 |
| 6,120,468 | A | 9/2000 | Tseng |
| 6,151,402 | A | 11/2000 | Azima et al. |
| 6,175,981 | B1 | 1/2001 | Lizama et al. |
| 6,231,497 | B1 | 5/2001 | Souder |
| 6,377,145 | B1 | 4/2002 | Kumagai |
| 6,502,264 | B1 | 1/2003 | Clothier et al. |
| 6,659,773 | B2 | 12/2003 | Roy et al. |
| 6,694,035 | B1 | 2/2004 | Teicher et al. |
| 6,763,532 | B2 | 7/2004 | Gardenier et al. |
| 6,785,922 | B2 | 9/2004 | Bretschger et al. |
| 6,798,888 | B1 | 9/2004 | Howarth et al. |
| 6,953,439 | B1 | 10/2005 | Kabemba |
| 6,957,454 | B1 | 10/2005 | Newton |
| 6,984,057 | B1 | 1/2006 | Rogers |
| 7,081,083 | B2 | 7/2006 | Ardizzone |
| 7,082,368 | B2 | 7/2006 | Nickel |
| 7,082,395 | B2 | 7/2006 | Tosaya et al. |
| 7,082,570 | B1 | 7/2006 | von Wiegand et al. |
| 7,418,108 | B2 | 8/2008 | Oser |
| 7,553,288 | B2 * | 6/2009 | Cohen ............... 601/47 |
| 7,981,064 | B2 | 7/2011 | Oser et al. |
| 2002/0141610 | A1 | 10/2002 | Devantier et al. |
| 2004/0164971 | A1 | 8/2004 | Hayward et al. |
| 2005/0069166 | A1 | 3/2005 | Peng |
| 2005/0124897 | A1 | 6/2005 | Chopra |
| 2005/0154249 | A1 | 7/2005 | Ardizzone |
| 2006/0069327 | A1 * | 3/2006 | Sanada et al. ............ 601/58 |
| 2007/0041606 | A1 | 2/2007 | Sheppard, Jr. |
| 2009/0010468 | A1 | 1/2009 | Oser et al. |

OTHER PUBLICATIONS

U.S. Appl. No. 60/706,718, filed Aug. 9, 2005.
Non-Final Office Action mailed Aug. 31, 2010, in U.S. Appl. No. 11/463,520.
http://www.colic.com/Company.htm; Sweet Dreams, Inc., printed Jul. 29, 2006.
http://www.elixa.com/mattress/massagerplain.htm; Tranqil-Ease Mattress Massager, printed Jul. 29, 2006.
http://www.bme.vanderbilt.edu/King/sleepmate.htm;International Award-Winning Student invention Benefits Newborns; Jamie Iaown Reeves; The Vanderbilt Register, Jan. 19-25, 1998, p. 4.
http://www.cymatherapy.com/main-ancient-roots.html; Sound-from Ancient Roots to Modern Research, printed Jul. 29, 2006.
http://www.cymatherapy.com/main-new-wave.html; Cymatherapy: A New Wave in Sound Techniques, printed Jul. 29, 2006.
http://www.rolen-star.com; Rolen-Star Audio Transducers, printed Jan. 17, 2005.
http:/www.baudine.com/eric/bass/tactile_report.html; Transducer Comparison, printed Jan. 17, 2005.
Steven Ashley, Artificial Muscles, Scientific American, Oct. 2003, pp. 53-59.
Shelby Addison et al.; Sleep Monitoring; Duke University Smart House, Pratt School of Engineering; Spring 2005; pp. 1-5.

* cited by examiner

INDUCING TACTILE STIMULATION OF MUSICAL TONAL FREQUENCIES

CROSS REFERENCE TO RELATED APPLICATION

This application is a divisional application of U.S. patent application Ser. No. 11/463,520, entitled "System and Method for Integrating Transducers into Body Support Structures," by Richard Barry Oser, filed Aug. 9, 2006, which application is a continuation-in-part of U.S. patent application Ser. No. 11/061,924 entitled "Transducer for Tactile Applications and Apparatus Incorporating Transducers" by R. Barry Oser, filed Feb. 18, 2005, and claims the benefit of U.S. Provisional Application Ser. No. 60/706,718 entitled "A System and Method for Integrating Transducers into Body Support Structures" by R. Barry Oser and Suzannah Long, filed Aug. 9, 2005, the entire disclosures of which are hereby specifically incorporated by reference for all that they disclose and teach.

BACKGROUND OF THE INVENTION

Stress is a significant factor in modern society. Stress is an emotional, physical, and psychological reaction to change. For example, a promotion, a marriage, or a home purchase can bring a change of status and new responsibility, which leads to stress. Stress is an integral part of life.

According to recent American Medical Association statistics: over 45% of adults in the United States suffer from stress-related health problems; 75-90% of all visits to primary care physicians are for stress-related complaints and disorders; every week 112 million people take some form of medication for stress-related symptoms; and on any given day, almost 1 million employees are absent due to stress. In view of this, it is clear that there is a need for improved means for stress reduction.

It has been found that certain types of relaxation help in reducing stress. In the alpha-theta states, people can reduce stress levels, focus, and be centered, i.e., not lost in the emotion of the moment. In these states, people can be more creative and self-expressive and bring more clarity to all their ideas.

As the pace and stress of modern life has increased, research into the physical, mental and psychological benefits of stress reduction has also increased. Recently, research has centered on the positive impact of neuro-feedback (EEG Training). The recent availability of powerful personal computers has allowed widespread application of neuro-feedback techniques. Using feedback to increase the deeper, more relaxed brainwave states known as alpha and theta, in turn, facilitates the ability of the subject to understand the feeling of these states of reduced stress and emotionality. Practice with feedback devices allows a subject to access alpha and theta more readily when the states are needed and useful.

Feedback techniques may rely upon the use of tones or graphs on the computer screen to gauge access to the states. However, these desired states often are not easy to achieve unless the subject spends a lot of time in practice sessions.

Another known method of achieving stress reduction has been to provide physical relaxation inputs, such as sitting on a beach or having a full-body massage. However, providing these inputs is usually impractical when they are needed.

Therapeutic body support structures have the potential for providing physical relaxation inputs in a convenient manner to reduce stress. Numerous attempts have been made in the prior art at providing therapeutic body support structures such as chairs and tables that provide aural or vibratory stimuli. Examples include U.S. Pat. No. 2,520,172 to Rubinstein, U.S. Pat. No. 2,821,191 to Paii, U.S. Pat. No. 3,556,088 to Leonardini, U.S. Pat. Nos. 3,880,152 and 4,055,170 to Nohmura, U.S. Pat. No. 4,023,566 to Martinmaas, U.S. Pat. No. 4,064,376 to Yamada, U.S. Pat. No. 4,124,249 to Abbeloos, U.S. Pat. No. 4,354,067 to Yamada et al., U.S. Pat. No. 4,753,225 to Vogel, U.S. Pat. Nos. 4,813,403 and 5,255,327 to Endo, U.S. Pat. No. 4,967,871 to Komatsubara, U.S. Pat. No. 5,086,755 to Schmid-Eilber, U.S. Pat. No. 5,101,810 to Skille et al., U.S. Pat. No. 5,143,055 to Eakin, U.S. Pat. No. 5,624,155 to Bluen et al., U.S. Pat. No. 6,024,407 to Eakin and U.S. Pat. No. 5,442,710 to Komatsu.

SUMMARY OF THE INVENTION

An embodiment of the present invention may therefore comprise a method of inducing tactile stimulation to a user through a cushioned transducer interface using musical tonal frequencies comprising: placing higher frequency transducers in a region of the cushioned transducer interface that induces the tactile stimulation to upper portions of a body of the user with the musical tonal frequencies; placing lower frequency transducers in a region of the cushioned transducer interface that induces the tactile stimulation to lower portions of the body of the user with the musical tonal frequencies; applying the musical tonal frequencies to the higher frequency transducers and the lower frequency transducers; providing controls to the user that allow the user to separately alter the intensity of the musical tonal frequencies to the higher frequency transducers and the lower frequency transducers.

An embodiment of the present invention may further comprise a method of inducing tactile stimulation of musical tonal frequencies in a foam layer of a cushioned transducer interface comprising: providing a transducer that generates vibrations in response to a signal that is encoded with the musical tonal frequencies; providing a diaphragm that is mechanically coupled to the transducer so that the vibrations are transferred from the transducer to the diaphragm; placing the diaphragm in contact with the foam layer to transfer the vibrations from the diaphragm to the foam layer to induce the tactile stimulation to a user.

An embodiment of the present invention may further comprise a method of inducing tactile stimulation of musical tonal frequencies in a coil spring of a cushioned transducer interface comprising: providing at least one transducer that generates vibrations in a first predetermined frequency range in response to a signal that is encoded with the musical tonal frequencies; providing a diaphragm that is mechanically coupled to the transducer so that the vibrations are transferred from the transducer to the diaphragm; placing the transducer in an interior portion of the coil spring; coupling the diaphragm to the coil spring to transfer the vibrations from the diaphragm to the coil spring and to the cushioned transducer interface.

An embodiment of the present invention may further comprise a method of inducing tactile stimulation of musical tonal frequencies using a rigid diaphragm structure comprising: providing the rigid diaphragm structure; forming at least one first curved structure in a portion of the rigid diaphragm structure, the first curved structure having a curvature and thickness that causes the first curved structure to respond to a first set of predetermined musical tonal frequencies; forming at least one second curved structure in a portion of the rigid diaphragm structure, the second curved structure having a curvature and thickness that causes the second curved structure to respond to a second set of predetermined musical tonal frequencies; attaching a first transducer to the rigid diaphragm structure that vibrates in a frequency range that corresponds to the first set of predetermined frequencies; attaching a second transducer to the rigid diaphragm structure that vibrates in a frequency range that corresponds to the second set of frequencies.

An embodiment of the present invention may further comprise a method of inducing tactile stimulation of musical tonal frequencies in a transducer interface comprising: providing an electro-active polymer matrix array, the electro-active polymer array having a plurality of matrix array elements having predetermined shapes that are connected; providing electrical connections to the plurality of matrix array elements; disposing the electro-active matrix array in the transducer interface so that tactile stimulation of musical tonal frequencies can be induced in the transducer interface.

An embodiment of the present invention may further comprise a method of inducing tactile stimulation in a transducer interface that is disposed in a cast comprising providing a flexible material that includes an electro-active polymer matrix array; wrapping an area of a broken bone with the flexible material; applying a cast over the area of the broken bone and the flexible material; providing electrical connections to the electro-active polymer matrix array so that electrical signals can be applied to the electro-active polymer matrix array to induce tactile stimulation in the area of the broken bone.

DETAILED DESCRIPTION OF THE EMBODIMENTS

According to an embodiment of the present invention, transducers and resonators are embedded in body support structures to contact a user through a transducer interface for the purpose of conveying sound energy in the form of musical tonal frequencies to a user's body by distributing selected frequencies in selected spatial patterns. Body support structures comprise beds, pillows, chairs, mats, pads, tables and other structures typically used to support people. The sound may include various audio tones and/or music.

Figure 1:
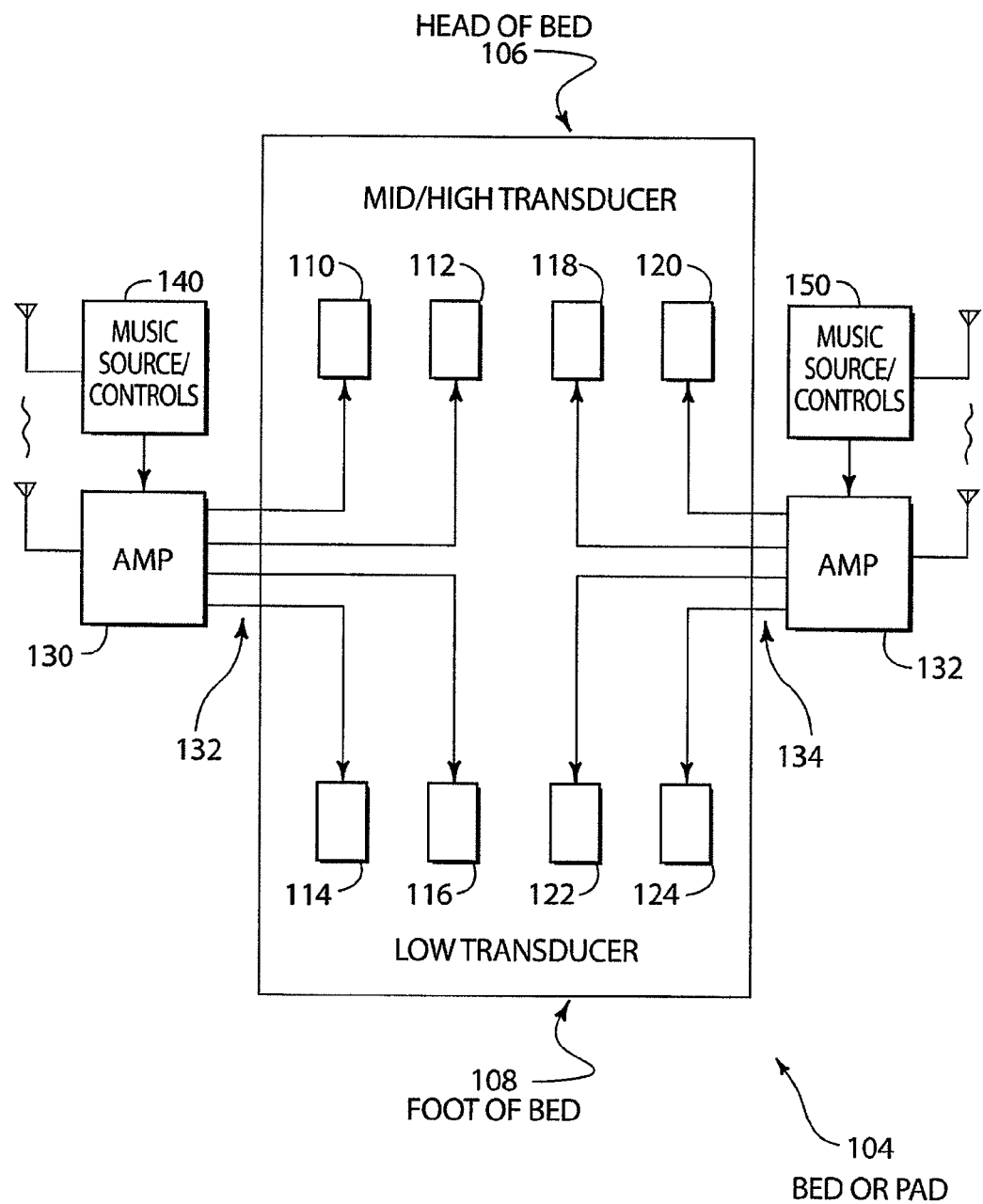
FIG. 1 illustrates a system in which multiple transducers and amplifiers are used to provide audio signals to a bed according to an embodiment of the present invention.

FIG. 1 is a schematic block diagram of the manner in which transducers can be placed in bedding or pads of various types for the transmission of music tones to a user's body. As will be appreciated by those skilled in the art, transducer interfaces can be used not only in beds, but in pads or pillows that fit over the beds, massage tables, chairs, lounge chairs, car seats, and airplane seating or just by themselves. Cushioned transducer interfaces can be made in different sizes and thicknesses. As shown in FIG. 1, a bed or pad 104 (cushioned transducer interface) has a series of mid to high frequency transducers 110, 112, 118, 120 disposed at a location that is proximate to the head of the bed or pad 106. In addition, a series of low frequency transducers 114, 116, 122, 124 are disposed at a location that is proximate to the foot of the bed 108. Of course, the location of the transducers can be shifted either up or down along the length of the bed to achieve the most desirable results for inducing music tonal frequencies into a user's body. On larger beds, such as shown in FIG. 1, two separate amplifiers 130, 132 and separate controls 140, 150 can be used to induce and control the music tonal frequencies in the transducers. For example, amplifier 130 operates in response to the control 140 that controls the application of music tonal frequencies to the amplifier 130. This can be achieved by using a hard wired control, or a wireless control, as schematically illustrated in FIG. 1. The wireless control can use RF signals, IR signals, etc. Control 140 supplies the source of music, and controls the application of the source of music to the amplifier 130. Similarly, the control unit 150 supplies music to amplifier 132 either over a hard wired connection or through a wireless connection, such as described above. Amplifiers 130, 132 amplify the music signal and apply electrical control signals 132, 134 to the transducers 110, 112, 118, 120, 114, 116, 122, 124. These transducers can comprise various types of transducers including transducers that are coupled to diaphragms, transducers that are embedded in foam, transducers that are embedded in the springs of a spring mattress or electro-active polymers, all of which are described in more detail below. In that regard, one type of transducer that can be used is disclosed in U.S. patent application Ser. No. 11/061,924 filed by Barry Oser entitled "Transducer for Tactile Applications and Apparatus Incorporating Transducers" which is specifically incorporated herein by reference for all that it discloses and teaches. Of course, any number of transducers can be used in the bed or pad 104.

Referring again to FIG. 1, in an embodiment of the present invention, amplifiers 130 and 132 are adapted to provide an external output port for headphones or plug and play speakers. The output of the transducers and the external output port can be separately controlled.

Figure 2:
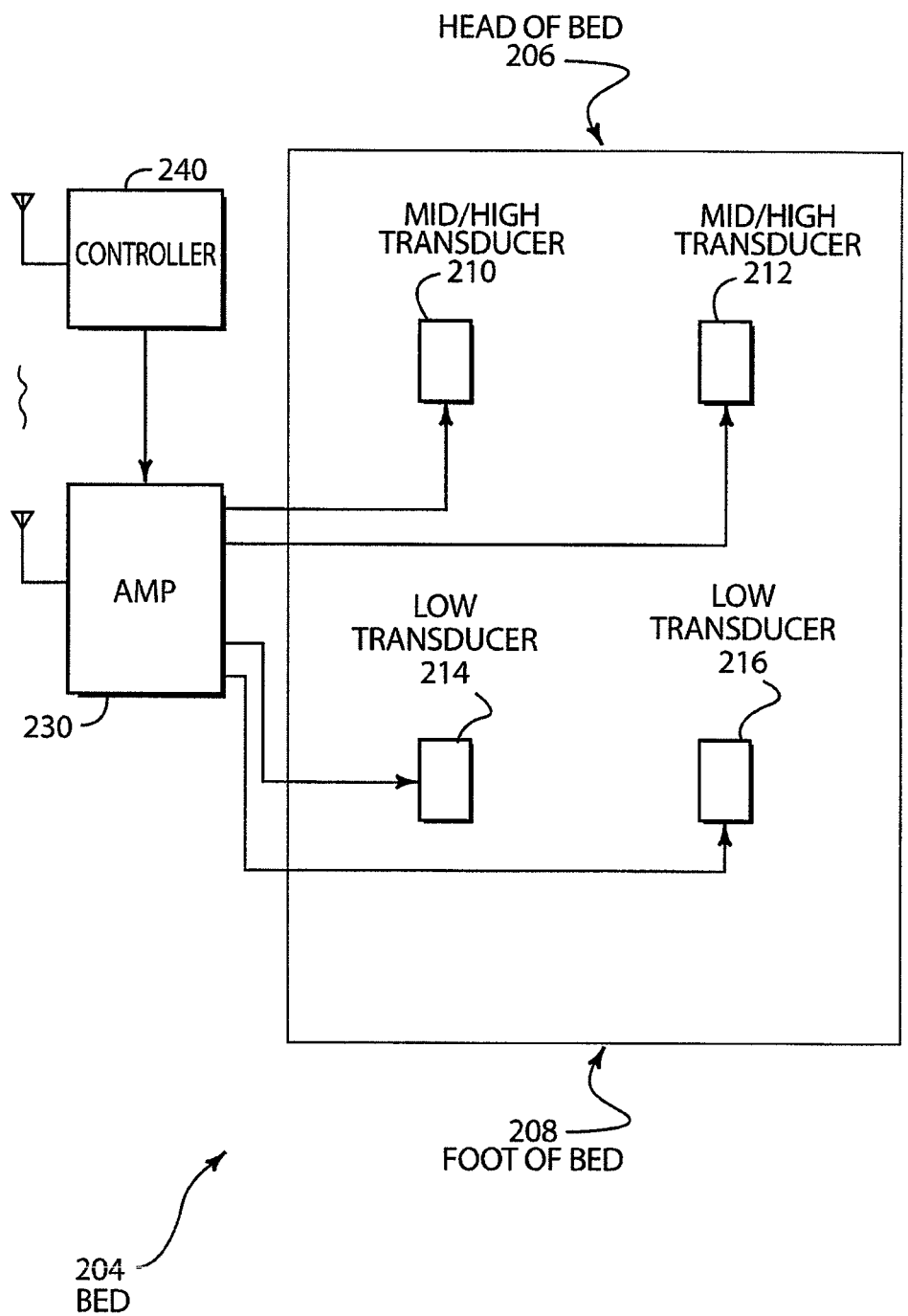
FIG. 2 illustrates a system in which multiple transducers and a single amplifier are used to provide audio signals to a bed according to an embodiment of the present invention.

FIG. 2 is a schematic illustration of the manner in which musical tonal frequencies can be applied to transducers in a smaller bed or pad 104. As illustrated in FIG. 2, four transducers 210, 212, 214, 216 are disposed in the bed or pad 204.

Again, these transducers can be any desired type of transducers such as described above. As shown in FIG. 2, transducers 210, 212 are mid to high range transducers. Transducers 214, 216 can comprise low frequency transducers. Amplifier 230 receives a musical signal from the controller 240 through either a wired connection or a wireless connection and generates control signals that are applied to the transducers 210-216. Again, any number of transducers can be used in the embodiment of FIG. 2.

Figure 3:
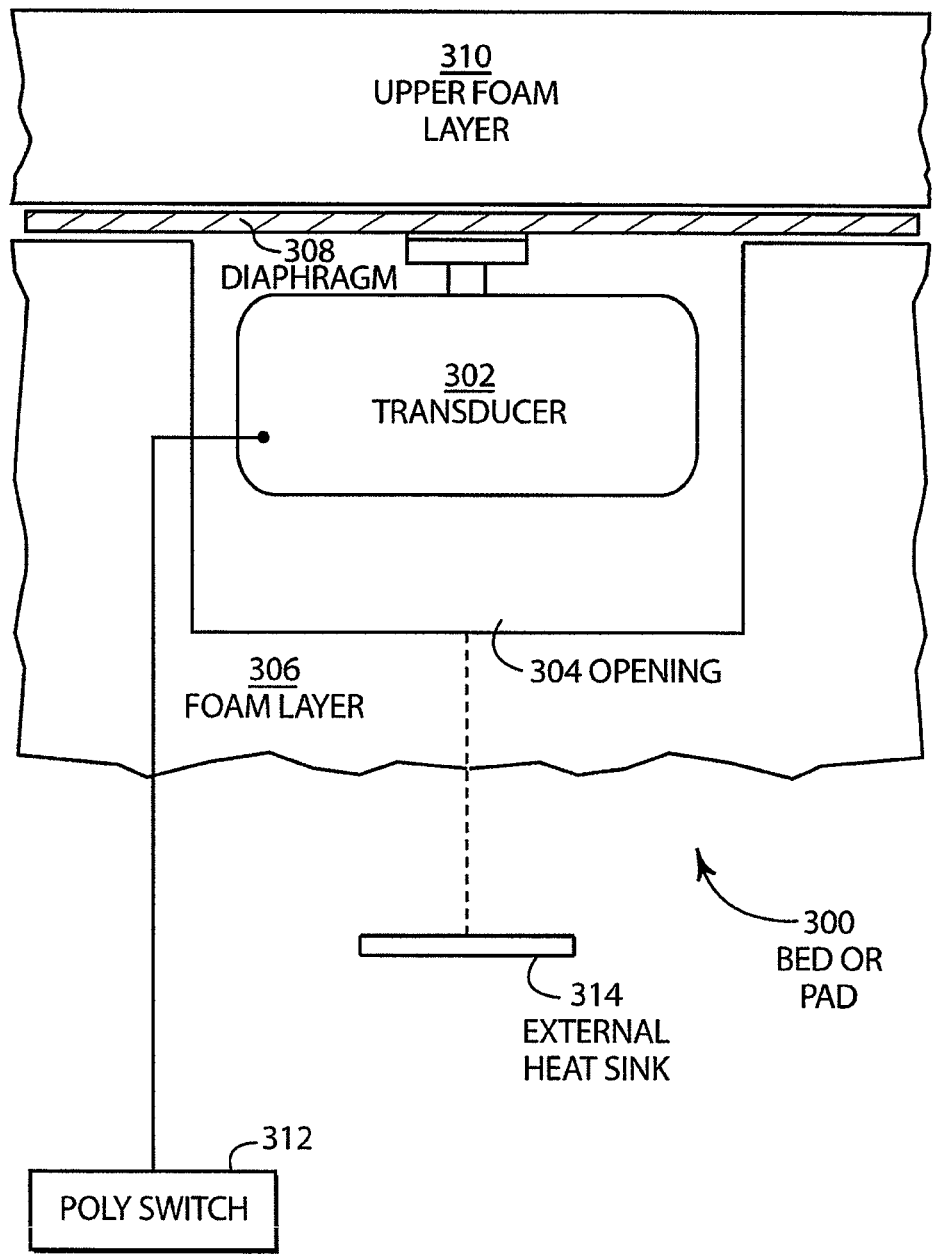
FIG. 3 illustrates a close up view of a system in which multiple transducers are installed in foam of a bed according to an embodiment of the present invention.

FIG. 3 is a schematic cutaway elevation of one embodiment for embedding a transducer in a bed or pad 300. The transducer 302 can be a transducer such as disclosed in the above identified patent application entitled "Transducer for Tactile Applications and Apparatus Incorporating Transducers", Ser. No. 11/061,924, which has been specifically incorporated herein by reference. As shown in FIG. 3, transducer 302 is disposed in an opening 304 of a foam layer 306 of bed or pad 300. The transducer 302 is mechanically coupled to a diaphragm 308. Diaphragm 308 extends outwardly from the opening 304 and engages the foam layer 306 along the outer edges of the diaphragm 308. In addition, diaphragm 308 is in contact with an upper foam layer 310. As an electrical signal is applied to the transducer 302, the transducer vibrates in response to musical tonal frequency and transmits those vibrations to the diaphragm 308. The diaphragm 308 is in contact with the upper foam layer 310 and the foam layer 306 (collectively referred to as cushioned transducer interfaces) and transmits the musical tonal frequencies to foam layer 306 and upper foam layer 310. Latex foam has been found to transmit the musical tonal frequencies efficiently to the user, but any desired type of foam can be used. Transducers placed in foam may cause a heat buildup. According to an embodiment of the present invention, heat build-up is managed by a temperature shut-off switch incorporated into a transducer. By way of illustration and not as a limitation, a poly-switch 312 may be used that turns off the transducer when it reaches a predetermined temperature. In an alternate embodiment of the present invention, an external heat-sink 314 may be placed in contact with a transducer to draw the heat away from the inside of the bed or to another area inside the bed to keep the temperature at an acceptable level.

Figure 4:
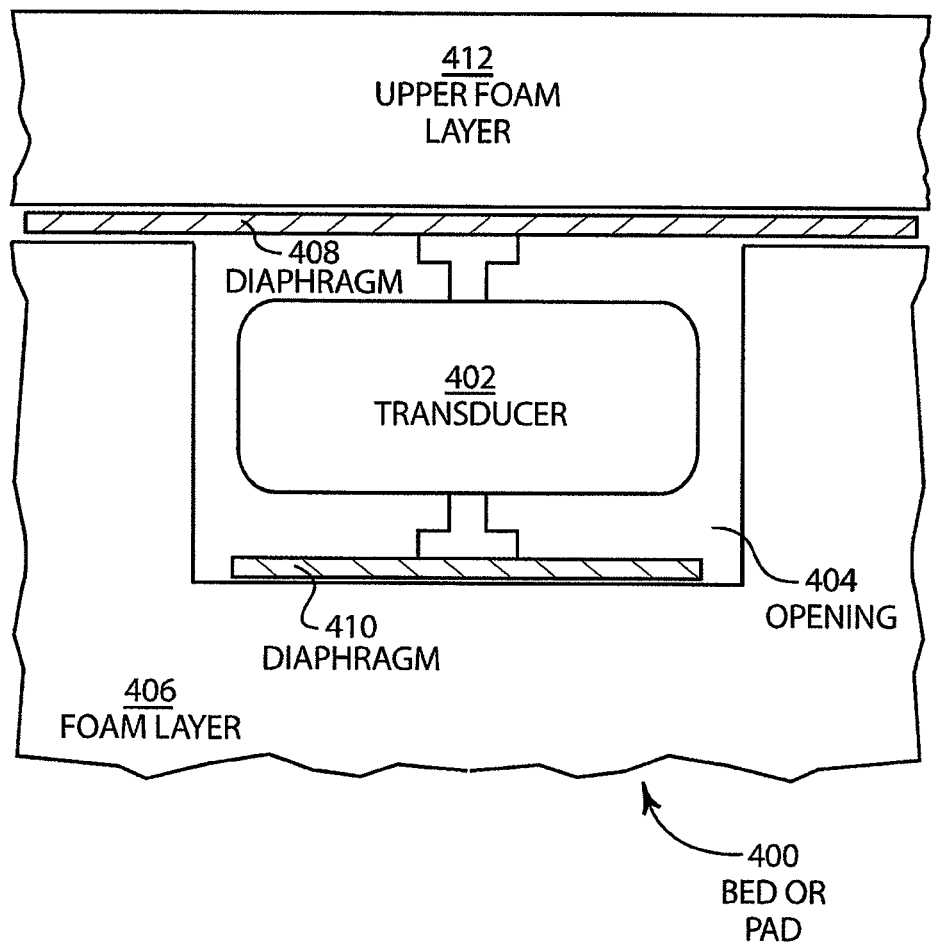
FIG. 4 illustrates a wellness stimulation system comprising a bed equipped with transducers and sensors according to an embodiment of the present invention.

FIG. 4 illustrates another embodiment of a bed or pad 400 (cushioned transducer interface) having a transducer 402 that is embedded in an opening 404 in foam layer 406. Transducer 402 is mechanically coupled to diaphragm 408 and diaphragm 410. Diaphragm 408 contacts the foam layer 406 along the outer edges of the diaphragm 408 and is in full contact with the upper foam layer 412. Diaphragm 410 rests on the bottom of the opening 404 to transmit vibrational waves into the foam layer 406. In addition, diaphragm 410 supports the transducer 402 in the opening 404. Musical tonal frequencies are applied to the transducer 402 which transmits the vibrational tonal frequencies to diaphragms 408, 410. The diaphragms 408, 410 transmit the musical tonal frequencies to upper foam layer 412 and foam layer 406.

Figure 5:
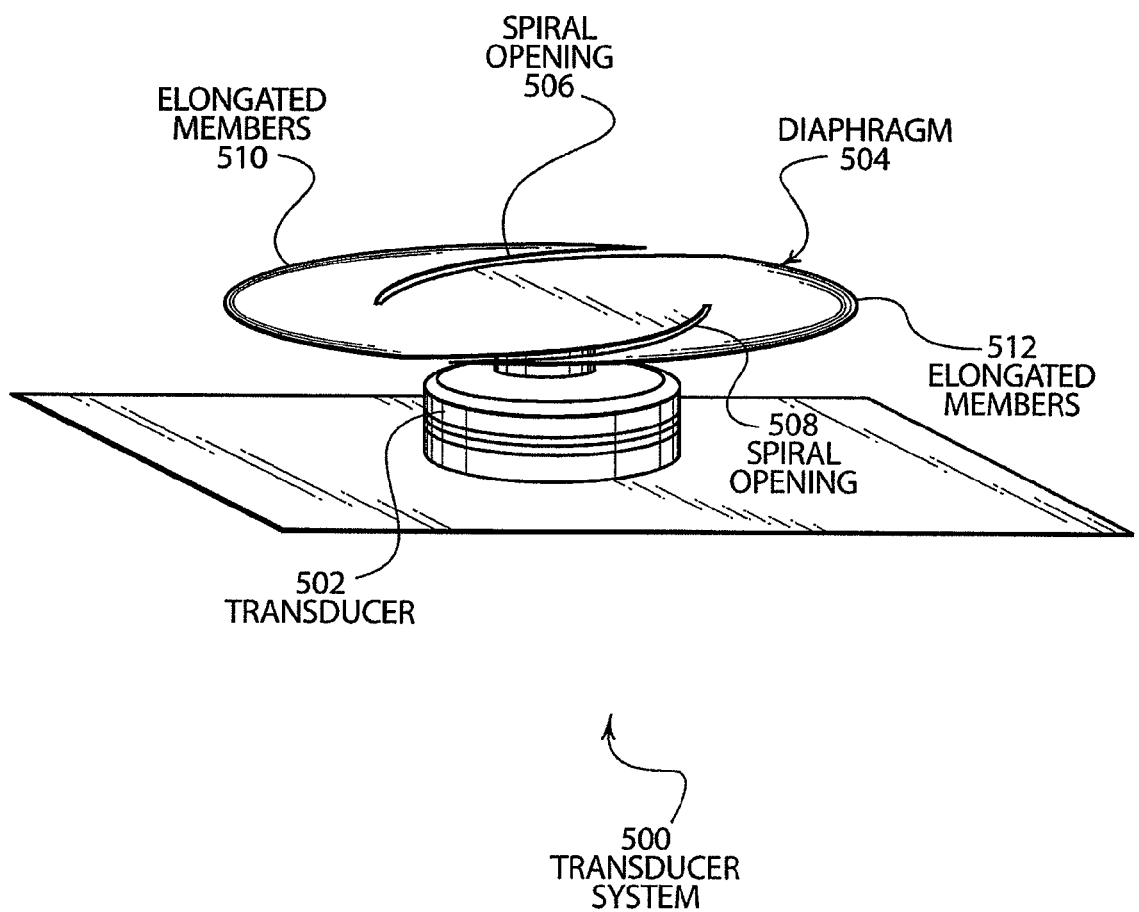
FIG. 5 is a schematic isometric view of an embodiment of a transducer system.

FIG. 5 is an isometric view of another embodiment of a transducer system 500. Transducer system 500 includes the transducer 502 that is coupled to the diaphragm 504. Diaphragm 504 can be made from a light, thin plastic material or composite such as a carbon fiber/Kevlar composite material. Plastics can include polycarbonate, polypropylene, polyethylene, or any other desired plastic material that is capable of transmitting the tonal frequencies of music through the diaphragm 504. As also shown in FIG. 5 spiral openings 506, 508 are formed in the diaphragm 504 to form elongated members 510, 512. The elongated members 510, 512 allow the diaphragm 504 to react to lower frequency inputs by the transducer 502. The elongated members 510, 512 also allow for flexibility of the diaphragm 504 which further increases the transfer of vibrational music tonal frequencies into the medium in which the diaphragm 504 is connected.

Figure 6:
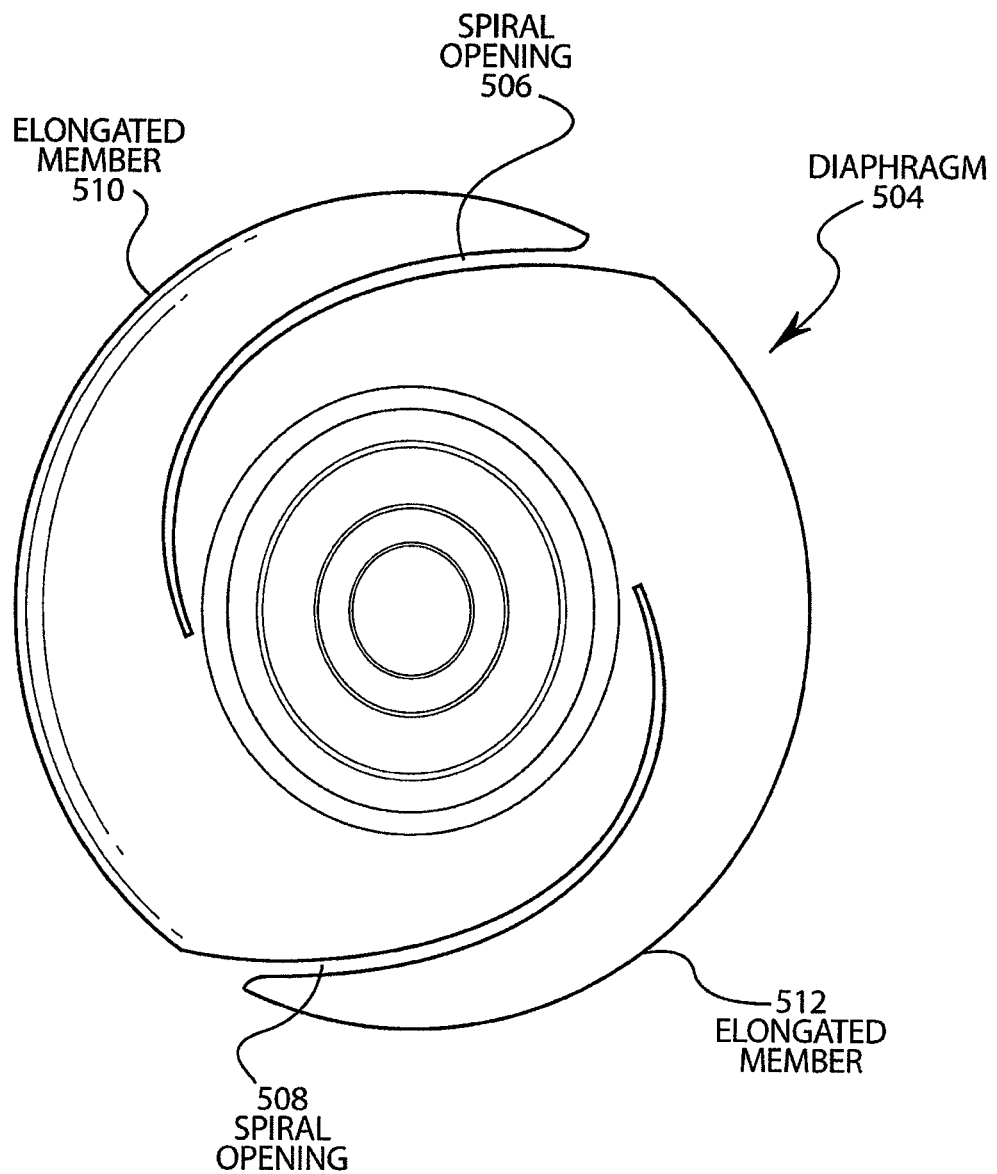
FIG. 6 is a schematic top view of an embodiment of a diaphragm of the transducer system of FIG. 5.

FIG. 6 is a top view of the diaphragm 504. As shown in FIG. 6, the diaphragm 504 has spiral openings 506, 508 formed on opposite sides of the diaphragm. Spiral openings 506, 508 form elongated members 510, 512 on opposite sides of the diaphragm 504. This creates a balanced structure for the diaphragm 504. The center structure of the diaphragm 504 provides a structural basis for supporting the diaphragm 504 and the elongated members 510, 512. The center portion can also function as an area for attachment of the diaphragm to a spiral spring as disclosed below with respect to FIG. 8.

Figure 7:
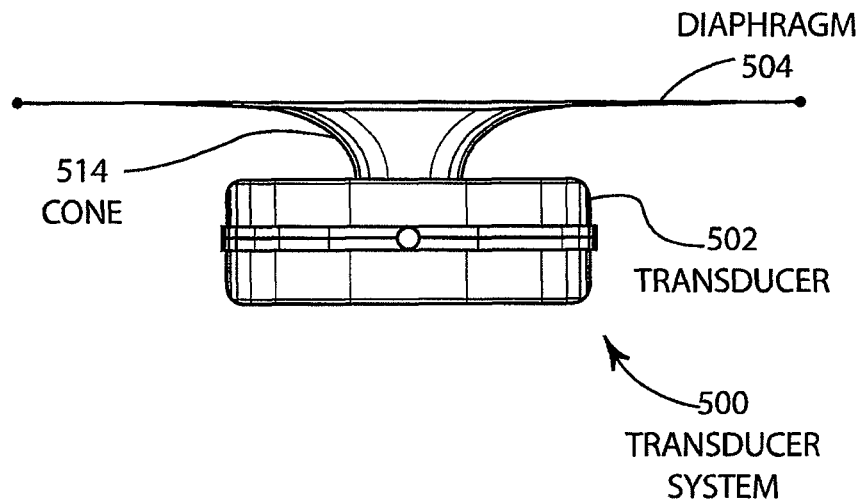
FIG. 7 is a schematic side view of the transducer system of FIG. 5.

FIG. 7 is a side view of the transducer system 500. Transducer system 500 includes the transducer 502 and the diaphragm 504. The diaphragm can be formed in a cone shape 514 in the area at which the diaphragm 504 is connected to the transducer 502. The cone 514 provides structural support to the diaphragm 504 and assists in transmitting the tonal frequencies from the transducer to the diaphragm 504.

Figure 8:
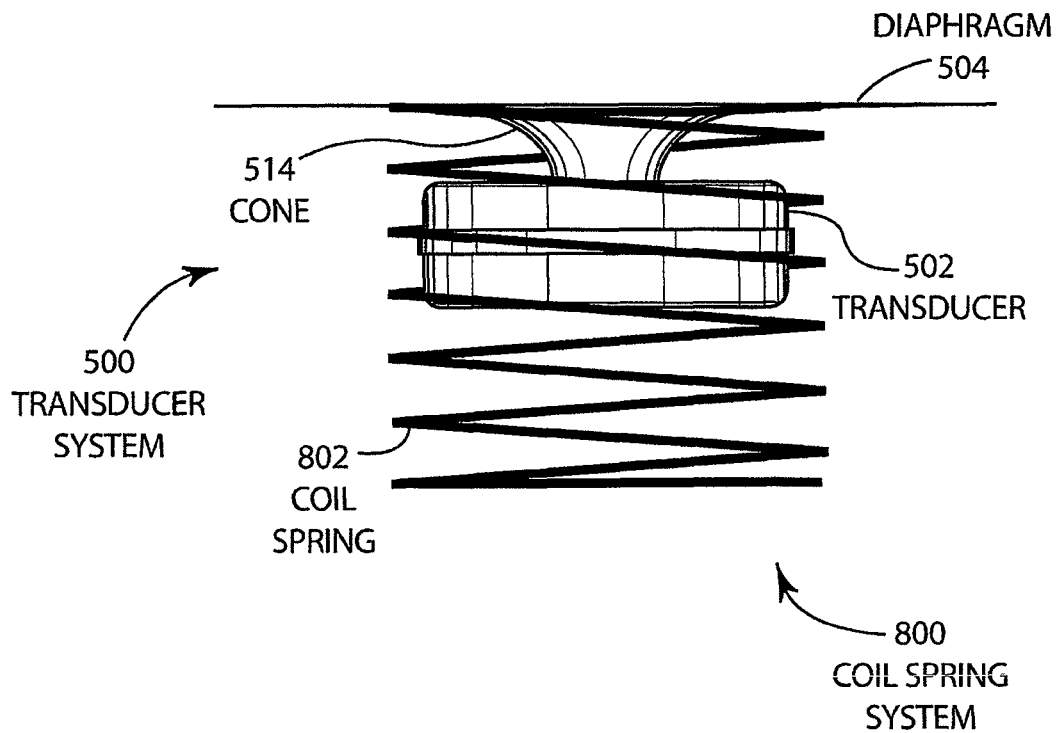
FIG. 8 is a schematic side view of an embodiment of a coil spring system.

FIG. 8 is a side view of a coil spring system 800 that connects a coil spring 802 to the transducer system 500. Transducer 502 is disposed in the interior portion of the coil spring 802. The diaphragm 504 is mechanically coupled to the coil spring 802 to transmit the vibrational tonal frequencies from the transducer 502 to the coil spring 802. The diaphragm 504 can have simple snap attachments that allow the diaphragm 504 to easily connect to the coil spring 802. In addition, a transducer 502 can be used that has a smaller diameter so that the coil spring 802 couples to the diaphragm 504 closer to the cone 514 to provide more structural rigidity at the point where the diaphragm 504 couples to the coil spring 802. Extended portions of the diaphragm 504 can be used to transmit vibrations into a foam layer overlaying the diaphragm 504. Special coil springs can be provided, if desired, during construction of a mattress that allow for insertion of transducers. In addition, the transducers can be constructed to couple directly to the existing coil springs so that specialized coil springs are not required. In addition, a customer can custom order a mattress that has the desired number of transducers which can be easily inserted in the coil springs during manufacture.

Figure 9:
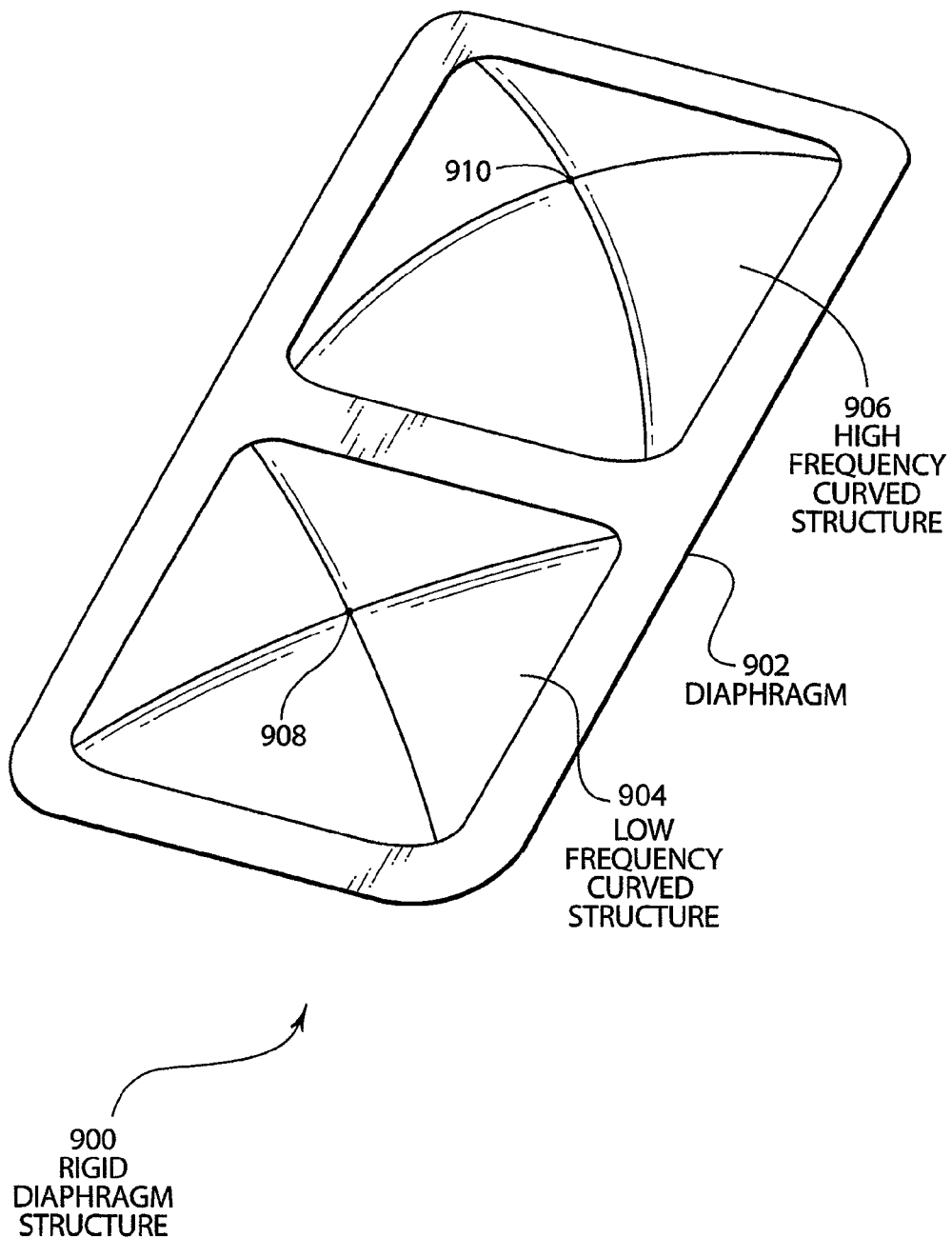
FIG. 9 is an isometric view of an embodiment of a rigid diaphragm structure.

FIG. 9 is a schematic isometric diagram of a rigid diaphragm structure 900. The rigid diaphragm structure 900 uses a single diaphragm 902 that has two separate curved structures 904, 906. Curved structure 904 responds to transducer vibrations at a lower frequency and has a predetermined curvature that is less than the curved structure 906. The curved structure 904 provides a certain rigidity to the diaphragm 902. The diaphragm 902 can be constructed of various materials such as a carbon fiber/Kevlar composite that may have a thickness of around one-quarter inch, curved wood panels, various stiff plastics such as polycarbonate and other plastic materials. The curved structures 904, 906 are empirically tuned to have a sympathetic frequency that is separated by a fourth on the music scale. Low frequency and high frequency transducers can be mounted at any point on the diaphragm 902 but are preferably mounted at center points or peaks 908, 910, respectively, to maximize the response of the diaphragm 902. In other words, if a high frequency transducer is mounted anywhere on the diaphragm 902, the high frequency transducer (not shown) will still create a resonance in the high frequency curved structure 906. Similarly, a low frequency transducer will create a resonance in the low frequency curved structure 904, no matter where it is mounted on the diaphragm 902. The tuning of the curved structures 904, 906 is created by the curvature and thickness of the diaphragm 902. The curvature creates a stiffness in the diaphragm 902 which varies the pitch. In other words, a greater curvature will create greater stiffness so that the more the structure is curved the higher the pitch. For example, as shown in FIG. 9, the curved structure 906 has more curvature than curved structure 904, so that curved structure 906 responds to higher frequencies than curved structure 904. In addition, the thickness of the diaphragm 902 adjusts the pitch of the curved structures 904, 906. Thinner materials respond to lower frequencies because the thinner materials can travel more easily for the excursions required at the lower frequencies. Again, the sympathetic frequencies of the curved structures 904, 906 are created on an empirical basis to create the fourth tonal differences on the music scale. For example, if the diaphragm 902 is 40 inches wide and approximately 80 inches long, a curvature of the low frequency curved structure 904 of approximately 1.25 inches and a curvature of the high frequency curved structure 906 of 1.75 inches, for a quarter-inch thick carbon fiber/Kevlar diaphragm creates the fourth tonal frequencies desired. For example, low frequency curved structure 904 may create a tone equivalent to "So" on the music frequency scale while high frequency curved structure 906 may create a tone "Do" above "So". The curved structures 904, 906 can be created by molding the diaphragm 902 in a simple heated mold. Curvatures in the range of approximately 1 inch to 2.5 inches creates the desired frequency responses.

Figure 10:
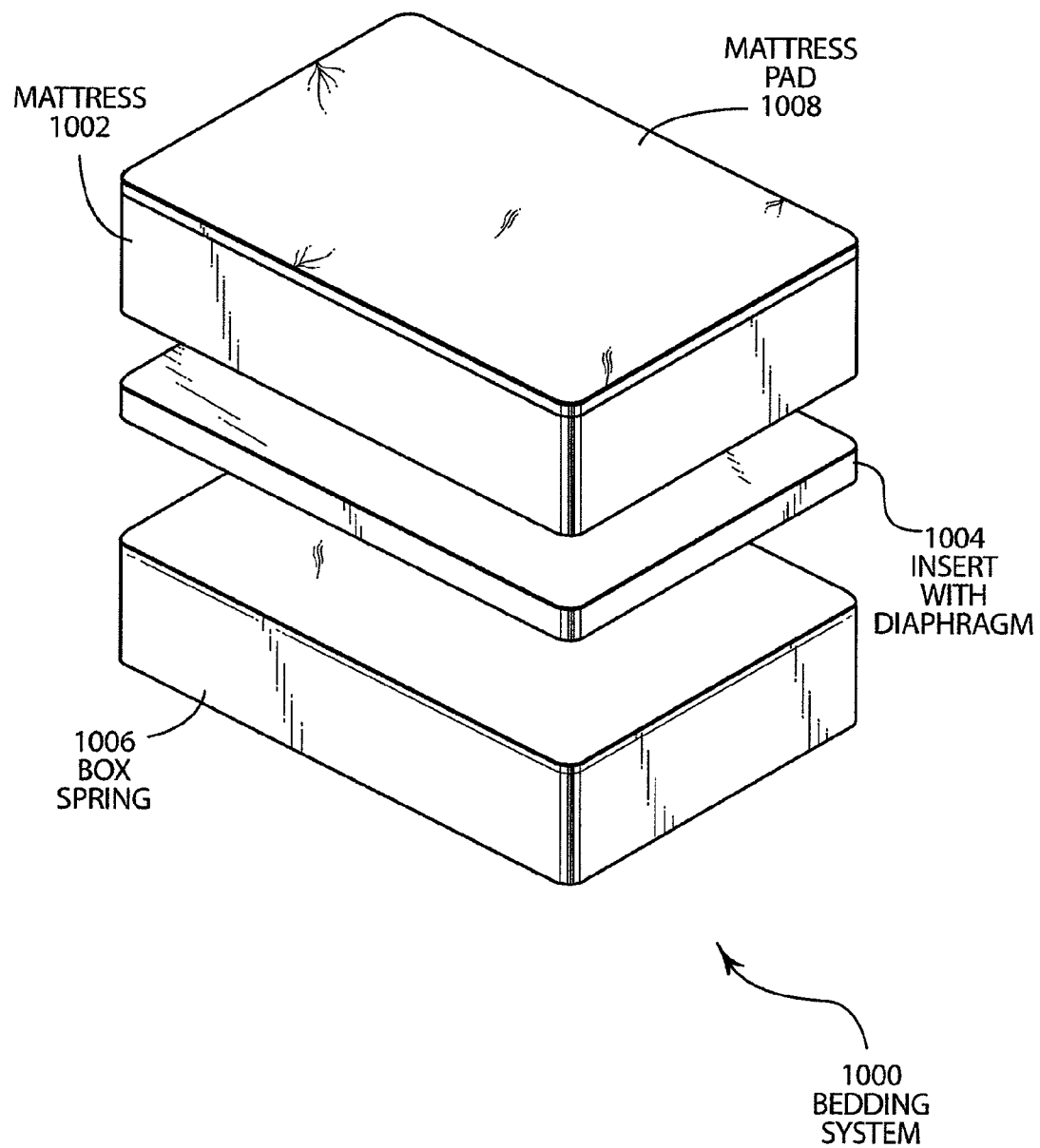
FIG. 10 is a schematic isometric view of an embodiment of a bedding system.

FIG. 10 is a schematic illustration of a bedding system 1000. In accordance with the embodiment of FIG. 10, a typical bedding system has a mattress 1002 and a box spring 1006. Disposed between the mattress 1002 and the box spring 1006 is an insert 1004 that includes a diaphragm. The diaphragm can comprise a coil spring transducer system such as illustrated in FIG. 8, or a rigid diaphragm structure 900 such as illustrated in FIG. 9. Further, transducers, such as transducer 302 (FIG. 3) and transducer 402 (FIG. 4), can be placed in the insert 1004 in a transverse direction and coupled to the structure of the insert 1004 to produce transverse motion of the insert diaphragm 1004. Such transverse motions have been found to induce relaxation in a very effective manner. Of course, the rigid diaphragm structure 900 can be inserted in a mattress pad 1008 to effectively transmit musical tonal frequencies to the user. For example, the rigid diaphragm structure 900 may be placed under a thin latex foam structure in the mattress pad 1008 to effectively transmit to separate tonal frequencies to the user through the mattress pad 1008.

Another type of transducer that can be used to transmit music and tones to the surface of the body is an electro-active polymers (EAPs). EAPs are disclosed in an article entitled "Artificial Muscles" by Steven Ashley, *Scientific American*, October 2003, pp. 53-59. Electro-active polymers are polymers that move in response to an electrical current. As disclosed in the *Scientific American* article, supra, "The fundamental mechanism underlying new artificial muscle products is relatively simple. When exposed to high-voltage electric fields, dielectric elastomers—such as silicones and acrylics—contract in the direction of the electric field lines and expand perpendicularly to them, a phenomenon physicists term Maxwell stress. The new devices are basically rubbery capacitors—two charged parallel plates sandwiching a dielectric material. When the power is on, plus and minus charges accumulate on opposite electrodes. They attract each other and squeeze down on the polymer insulator, which responds by expanding in area.

Engineers laminate thin films of dielectical elastomers (typically 30 to 60 microns thick) on the front and back with conductive carbon particles suspended in a soft polymer matrix. When connected by wires to a power source, the carbon layers serve as flexible electrodes that expand in area along with the material sandwiched in the middle. This layered plastic sheet serves as the basis for a wide range of novel actuation, sensory and energy-generating devices.

Dielectric elastomers, which can grow by as much as 400 percent of their nonactivated size, are by no means the only types of electroactive materials or devices, although they represent some of the more effective examples."

Electro-active polymers can be constructed as diaphragm actuators that are made by stretching the dielectric elastomer films over an opening in a rigid frame. Typically, the membrane is biased in one direction so that upon actuation, the membrane moves in that direction, rather than simply wrinkling. By using one or more diaphragms in this fashion, that respond to electrical currents, a tactile transducer can be produced for transmitting tactile information to a user's body. These transducers can be disposed in various types of transducer interfaces including mattress pads, yoga pads, shoes, elastic bandages such as Ace bandages, various wraps and bandages, seat cushions, shoe pads, adhesive pads, and other surfaces that can be used as transducer interfaces. These transducer interfaces can be used, as disclosed above, to transmit tonal frequencies, including music, to a user's body, to assist in inducing relaxation.

In addition, patterns of compliant electrodes can be created on a polymer sheet. When high voltages of opposite polarities are applied to the electrodes, the electrodes attract and move towards each other forcing the soft elastomer outwardly from the electrodes. This causes the areas between the electrodes to become thicker, i.e., creates bulges.

Figure 11:
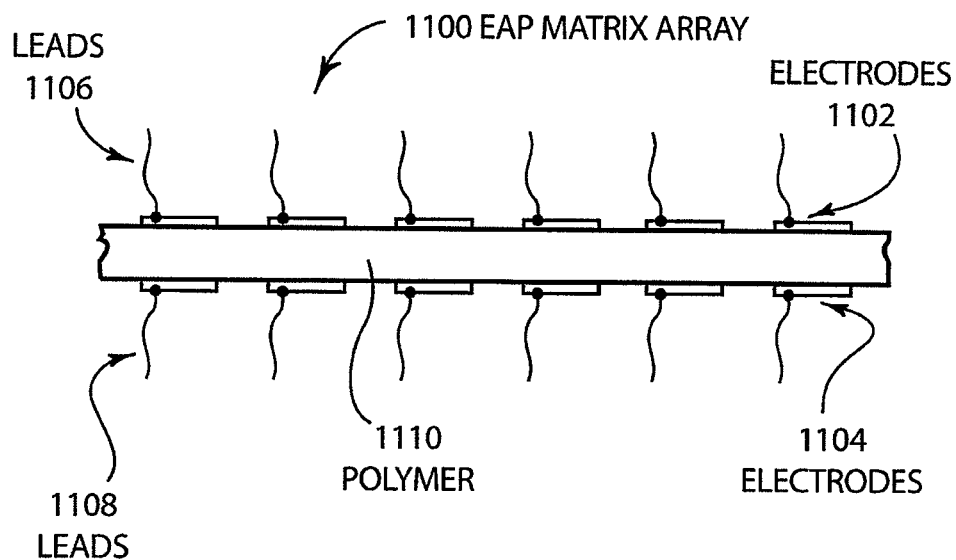
FIG. 11 is a schematic side view of an embodiment of an electro-active polymer matrix array.

FIG. 11 illustrates an electro-active polymer matrix array 1100. Polymer layer 1110 may have a thickness of approximately 30 to 60 microns. Electrodes 1102, 1104 are deposited on the surface of the polymer layer 1110. The electrodes 1102, 1104 are flexible electrodes that comprise conductive carbon particles that are suspended in a soft polymer matrix. Leads 1106, 1108 are connected to the electrodes 1102, 1104, respectively. A high voltage of opposite polarity is applied to leads 1106, 1108 which causes the electrodes 1102, 1104 to be attracted to each other. Electrodes 1102, 1004 can be made in any desired shape to produce the desired shape of the bulges of the EAP material.

Figure 12:
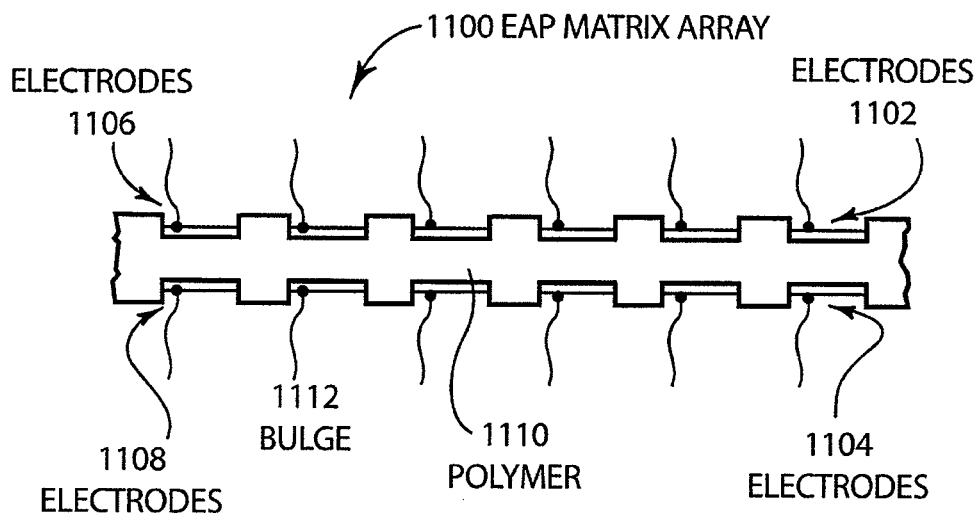
FIG. 12 is a side view of the electro-active polymer matrix array after voltage is applied to the electrodes.

FIG. 12 illustrates the EAP matrix array 1100 after a high voltage has been applied to leads 1106, 1108. As shown in FIG. 12, the electrodes 1102, 1104 are attracted towards each other and compress the soft polymer 1110. Electrodes 1102, 1104 actually move towards each other to move the soft polymer 1110. This compression and movement of the electrodes 1102, 1104, in response to the high voltage charges that accumulate on the electrodes 1102, 1104, causes the soft polymer 1110 to move outwardly from between the electrodes 1102, 1104. This causes the polymer 1110 to bunch up and create bulges, such as bulge 1112, between each of the electrodes.

The electrodes 1102, 1104 can form a two-dimensional matrix which results in a two-dimensional matrix of bulges that are capable of oscillating in accordance with the application of the high voltage electrical charge that is applied to the electro-active polymer matrix. Reasonably good frequency responses can be achieved with the electro-active polymer matrix, depending upon the particular polymer 1110 that is used. Frequency responses for transmitting music frequencies to users are achievable. Of course, different frequencies of the music can be applied to different portions of the electro-active polymer matrix array. Simple bandpass filters can be used to filter the input music, as illustrated in FIG. 13.

Figure 13:
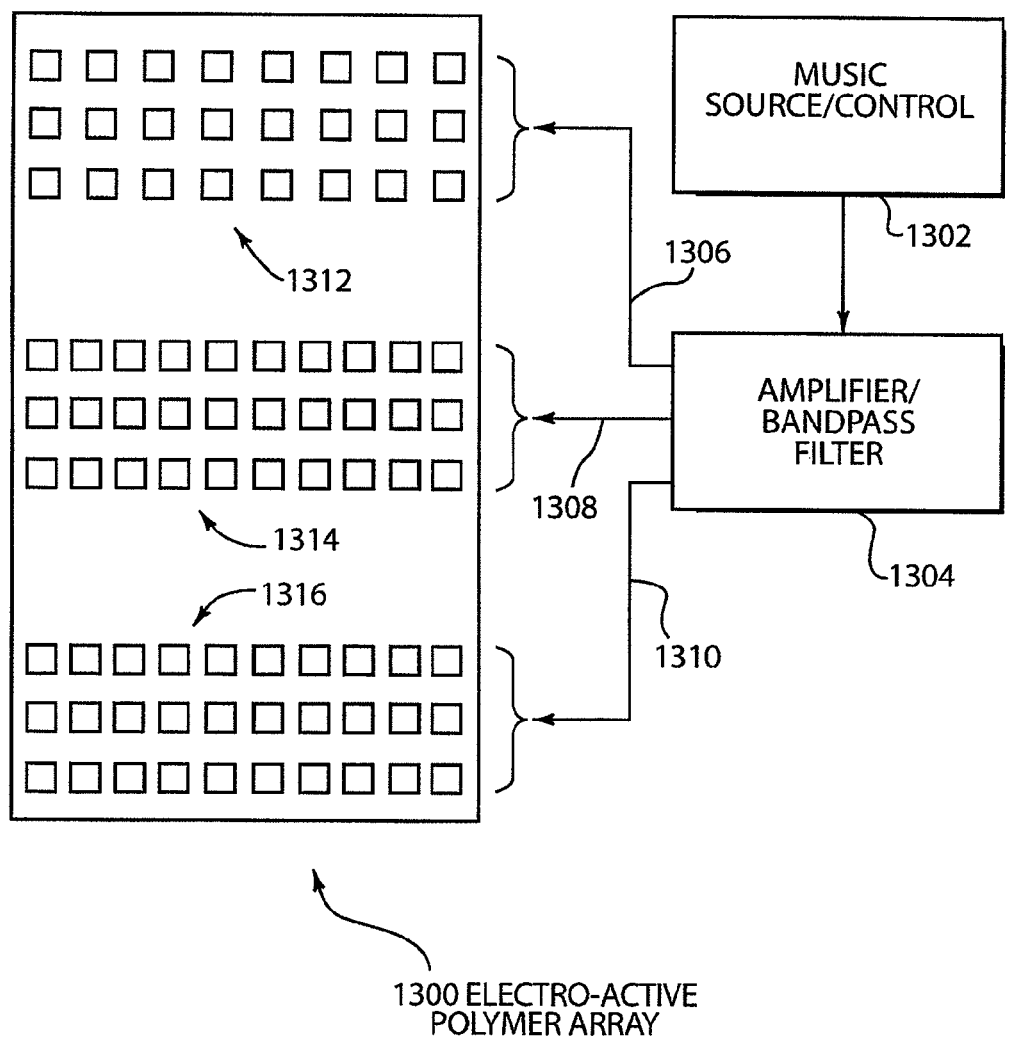
FIG. 13 is a schematic block diagram of an embodiment of an electro-active polymer array.

FIG. 13 illustrates the use of an electro-active polymer array 1300 in conjunction with a music source 1302 that is coupled to a bandpass filter/amplifier 1304. Music source 1302 generates music that is applied to the bandpass filter/amplifier 1304. Bandpass filter/amplifier 1304 amplifies the input signal and separates the input music into three separate frequency bands, a high band, a middle band and a low band. The amplifier of the bandpass filter/amplifier 1304 amplifies each of the bandpass signals to generate a series of three high voltage output control signals 1306, 1308, 1310 that are applied to different portions of the electro-active polymer array. For example, the high frequency, high voltage output signal 1306 is applied to a series of array elements 1312 that are located towards the head of the bed. Similarly, high voltage, mid frequency output signal 1308 is applied to a series of array elements 1314 that are located in the mid portion of the bed or pad 1302. Also, high voltage, low frequency output signal 1310 is applied to array element 1316 that is located at the foot of the bed or pad 1302. Of course, any desired distribution of frequencies can be applied in any desired manner. Multiple bandpass filters can be used to further divide the frequencies and apply those different frequencies to multiple portions of the electro-active polymer array transducer interface 1300.

Figure 14:
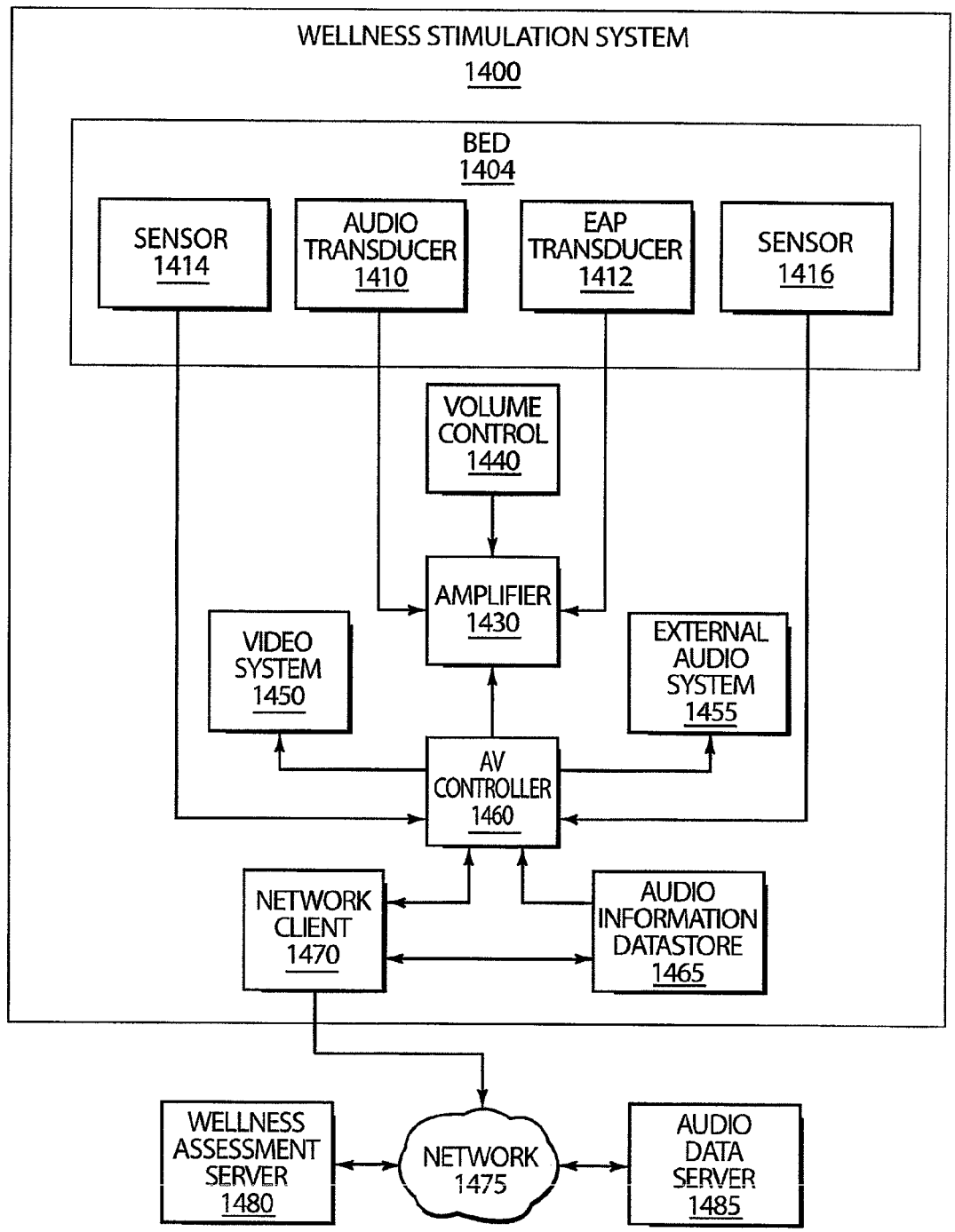
FIG. 14 is a schematic block diagram of a wellness simulation system.

FIG. 14 illustrates a wellness stimulation system comprising a bed equipped with transducers and sensors according to an embodiment of the present invention. Referring to FIG. 14, wellness stimulation system 1400 comprises bed 1404 that has an audio transducer 1410, EAP transducer 1412, and/or sensor 1414 and 1416. While various transducers are illustrated, any desired type of transducer can be used. As previously described, multiple sensors of each type may be used without departing from the scope of the invention.

Audio signals are fed to audio transducer 1410 and EAP transducer 1412 via amplifier 1430 under control of volume control 1440. The audio signals sent to amplifier 1430 are retrieved from audio information datastore 1465 by audio/video (AV) controller 1460. According to an embodiment of the present invention, AV controller 1460 is programmable and may select audio information based on pre-programmed instructions or in response to sensors 1414 and 1416.

Sensors 1414 and 1416 obtain physiological data from the user of bed 1404. By way of illustration, the sensors may detect heart rate, neurological data, and sounds produced by the body of the user. This data is fed to AV controller 1460. AV controller 1460 may utilize the data locally or send to the data via network client 1470 to a wellness assessment server 1480 via network 1475 for evaluation. As will be appreciated by those skilled in the art, network 1475 may be a private network or a public network such as the Internet. Further, wellness assessment server may evaluate the data received from sensors 1414 and 1416 in conjunction with a medical history of the user.

The wellness assessment server 1480 reports its results back to AV controller 1460, which uses the information to select audio information from audio information datastore 1465. According to another embodiment of the present invention, audio information datastore 1465 is periodically updated by audio data server 1485 via network 1475 and network client 1470. AV controller 1460 also connects to video system 1450 and external audio system 1455. Using these connections, AV controller 1460 may provide a user of bed 1404 external video and audio stimulation based on pre-programmed instructions, in response to data acquired by sensors 1414 and 1416, or based on user input. For example, the user input may be provided by a remote control, voice recognition, and/or wire connected control.

According to another embodiment, the AV controller 1460 further comprises a voice synthesizer to provide verbal feedback and information to a user. This information may provide encouragement, the results of the sensor analysis, and instruction to the user. Using the network connection, the wellness stimulation system 1400 may also allow a user to interact in real-time a doctor, therapist or healthcare giver. In this way, a user can obtain wellness assistance at any time. Moreover, the wellness stimulation system 1400 may be used in hospitals, residences, nursing homes for diagnostic analysis, and vibrational/sound/resonance delivery for any medical, musical, and or vibrational information.

In yet another embodiment of the present invention, the wellness stimulation system 1400 functions as an awakening system. In this embodiment, AV controller 1460 is programmed with a predetermined wake-time setting. AV controller 1460 maintains a time of day and continuously compares the predetermined wake-time setting with the present time-of-day. At the predetermined wake-time, AV controller 1460 generates a wake authorization signal, which can be sound, music, or video information, and communicates that signal to selected transducers, external audio devices, and external video devices. According to another embodiment of the present invention, the AV controller 1460 progressively increases the signal power of the wake authorization signal and may further add devices to which that signal is transmitted.

Figure 15:
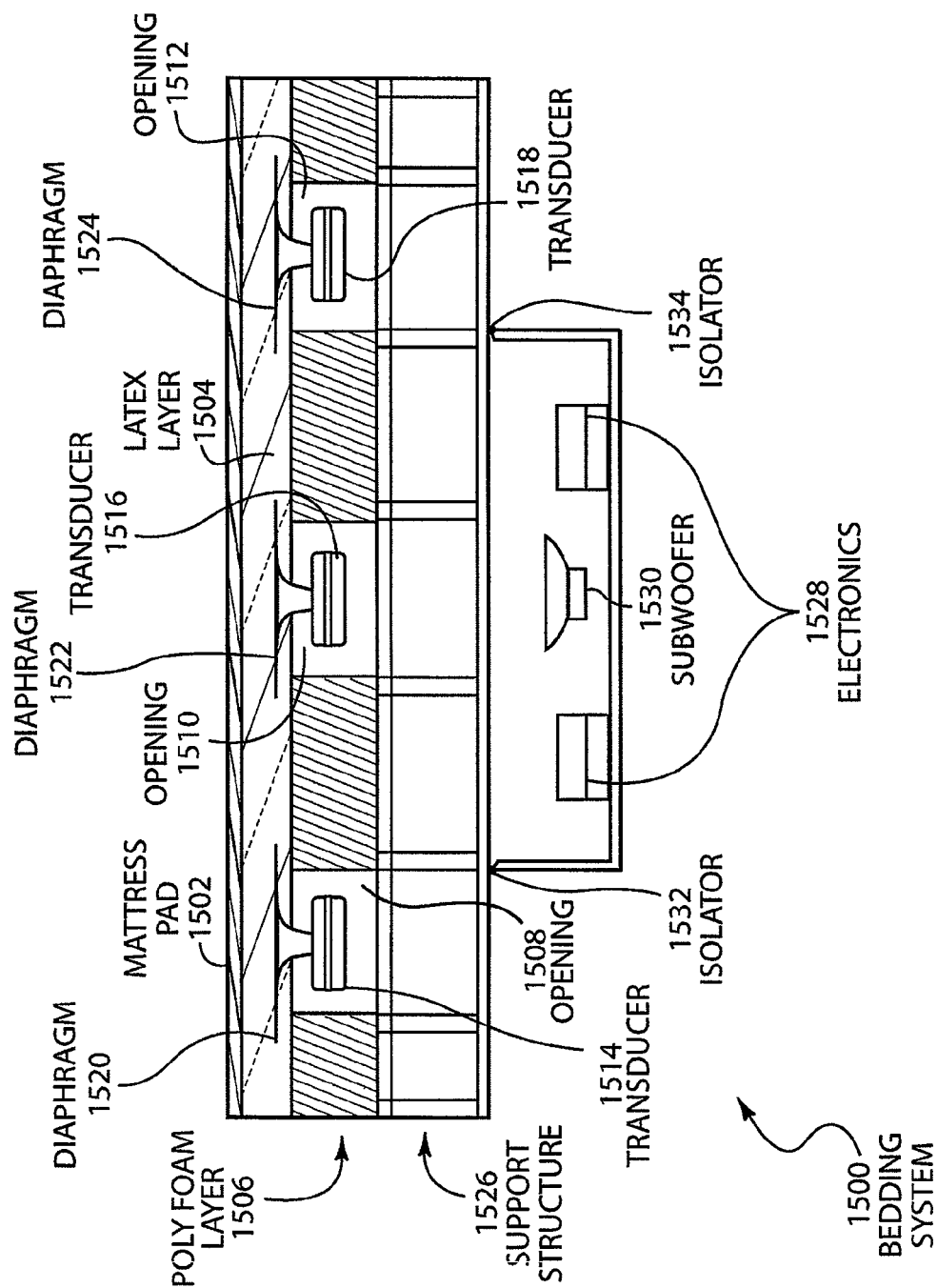
FIG. 15 is a schematic elevation view of an embodiment of a bedding system.

FIG. 15 discloses a bedding system 1500 using the structures of various embodiments disclosed above. As shown in FIG. 15, the bedding system 1500 includes a mattress pad 1502 that may comprise a standard mattress pad as used on typical mattresses. Below the mattress pad is a latex layer 1504. The latex layer is supported by a polyfoam layer 1506. Openings 1508, 1510, 1512 are formed in the polyfoam layer 1506. Transducers 1514, 1516, 1518 are disposed in the openings 1508, 1510, 1512, respectively. Diaphragms 1520, 1522, 1524 are coupled to the transducers 1514, 1516, 1518, respectively. The diaphragms 1520, 1522, 1524 are embedded in the latex layer 1504 to transmit the vibrational tonal frequencies into the latex layer 1504 and into the mattress pad 1502. A support structure 1526 is provided that supports the polyfoam layer 1506. The support structure 1526, for example, may comprise a box spring layer. Electronics 1528 and a subwoofer 1530 may be attached to the underside of the support structure 1526 by isolators 1532, 1534. Hence, the bedding system 1500 discloses an overall embodiment that employs various structures disclosed above that provides a bedding system 1500 that can transmit vibrational frequencies to a user.

Figure 16:
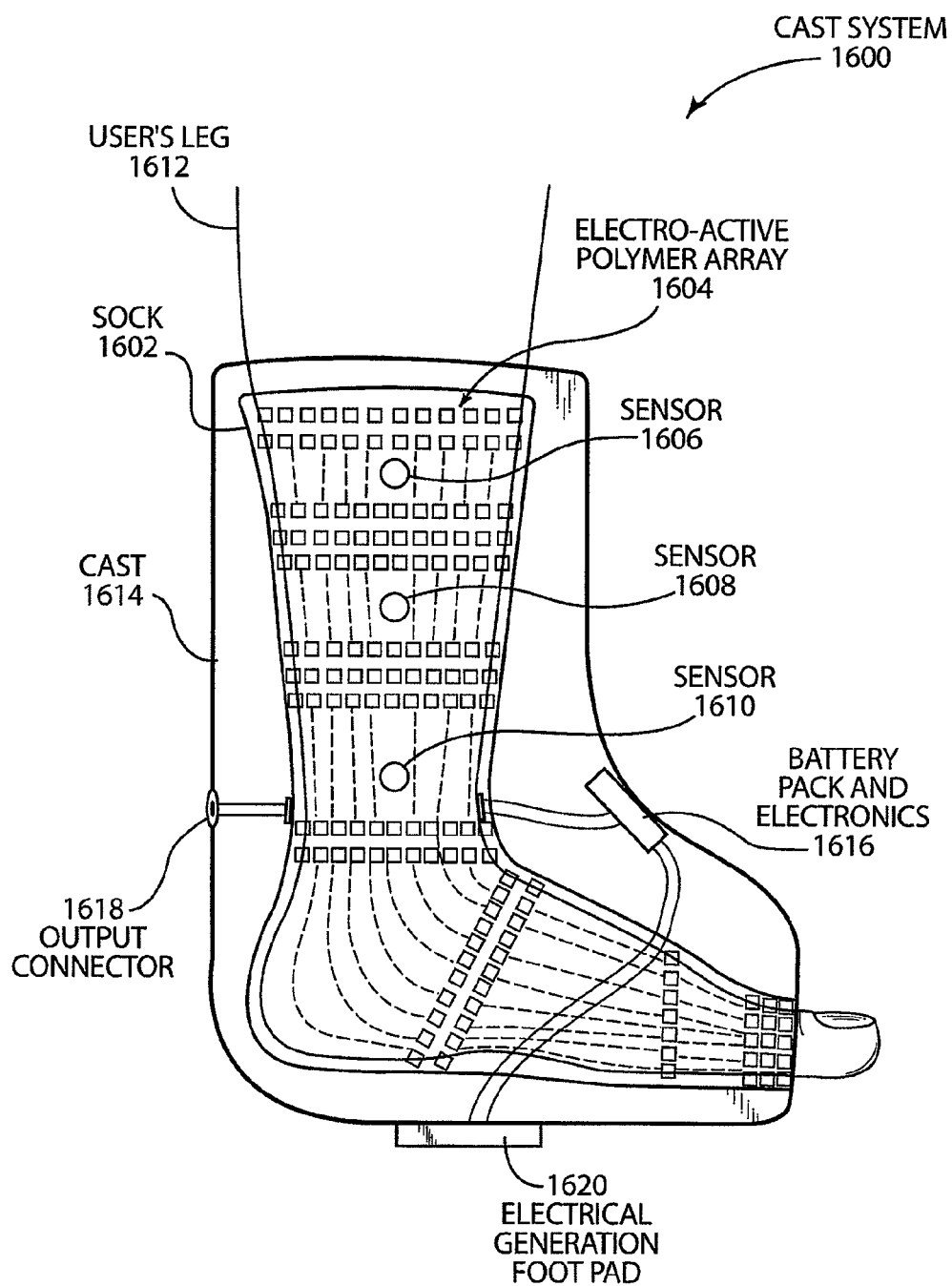
FIG. 16 is a schematic drawing of an embodiment of a cast for assisting healing.

FIG. 16 schematically illustrates a cast system 1600 for assisting the healing of a broken bone in the lower portion of a user's leg 1612. Of course, the techniques and systems illustrated in FIG. 16 can be used for various types of breaks and cast systems for other portions of the body and FIG. 16 is merely illustrative of the manner in which the cast system can be used to heal bones using the techniques illustrated in FIG. 16. As shown in FIG. 16, a sock 1602 is embedded with an electro-active polymer array 1604 and sensors 1606, 1608, 1610. The sock 1602 can be made of an electro-active polymer material or any other desired material such as an absorbent, soft material that can be used adjacent to the skin of the user's leg 1612. The electro-active polymer array 1604 can be embedded in the sock 1602 as well as sensors 1606-1610. The cast material 1614 that holds the broken bone in place is coated around the sock 1602 in the same manner as a standard cast. The electro-active polymer array 1604 may be disposed throughout the material of the sock 1602 as shown in FIG. 16 or simply in the area near the broken bone. Similarly, sensors 1606, 1608, 1610 are placed in an area near the broken bone. The electro-active polymer array 1604 can be coupled directly to a battery/electronics pack 1616, but is capable of generating tonal frequencies that are applied to the electro-active polymer array 1604 that assists the broken bone and healing. Further, the electro-active polymer array 1604 increases blood circulation in the user's leg 1612 which also assists in healing in blood flow. Output connector 1618 can be connected to the sensor 1606, 1608, 1610 to provide biometric readings of the area around the broken bone. This biometric data can include temperature readings, conductivity readings, sonograms and other information that may assist a doctor in evaluating the healing process. This information can also be transmitted to a wellness assessment server in accordance with a system such as disclosed in FIG. 14 to evaluate the healing process and potentially modify the tonal frequencies, including musical tonal frequencies, that are applied to the electro-active polymer array 1604. In that regard, the output connector 1618, is also coupled to the battery/electronics pack 1616 which includes a microprocessor for generating the tonal frequencies that are used to assist the healing of the broken bone in the user's leg 1612. Further, a foot pad 1620 can also be used with the cast system 1600 for generating electricity to charge the battery pack 1616. The electrical generation foot pad 1620 can comprise a electro-active polymer material which is capable of generating electricity or any other type of system that is capable of producing electricity including movement devices that create electricity.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of inducing tactile stimulation of musical tonal frequencies using a rigid diaphragm structure comprising:
providing said rigid diaphragm structure;
forming at least one first curved structure in a portion of said rigid diaphragm structure, said first curved structure having a curvature and thickness that causes said first curved structure to have a resonant, sympathetic frequency that responds to a first set of predetermined musical tonal frequencies;
forming at least one second curved structure in a portion of said rigid diaphragm structure, said second curved structure having a curvature and thickness that causes said second curved structure to have a resonant, sympathetic frequency that responds to a second set of predetermined musical tonal frequencies that is different from said first set of predetermined musical tonal frequencies;
attaching a first transducer to said rigid diaphragm structure that vibrates in a frequency range that corresponds to said first set of predetermined frequencies;
attaching a second transducer to said rigid diaphragm structure that vibrates in a frequency range that corresponds to said second set of frequencies.

2. The method of claim 1 further comprising:
forming additional curved structures in said rigid diaphragm structure that respond to additional sets of musical tonal frequencies.

3. The method of claim 2 further comprising:
attaching additional transducers to said rigid diaphragm structure that vibrate at frequencies that correspond to said additional sets of musical tonal frequencies.

4. The method of claim 1 wherein said process of attaching said first transducer to said rigid diaphragm structure and attaching said second transducer to said rigid diaphragm structure comprises:
attaching first transducer to said rigid diaphragm structure at a location that corresponds to a peak of said first curved structure;
attaching said second transducer to said rigid diaphragm structure at a location that corresponds to a peak of said second curved structure.

5. The method of claim 1 further comprising:
placing said rigid diaphragm structure as an insert between a box spring and a mattress to induce tactile stimulation of said musical tonal frequencies in a bedding system.

6. The method of claim 1 further comprising:
placing said rigid diaphragm structure in an insert to induce tactile stimulation of said musical tonal frequencies in said insert.

* * * * *